United States Patent [19]

Newton

[11] 4,022,814
[45] May 10, 1977

[54] IODINE CONTAINING ORGANIC CARBONATES FOR USE AS RADIOGRAPHIC AGENTS

[75] Inventor: Barry N. Newton, West Lafayette, Ind.

[73] Assignee: Lafayette Pharmacal, Inc., Lafayette, Ind.

[22] Filed: Apr. 22, 1976

[21] Appl. No.: 679,393

Related U.S. Application Data

[63] Continuation-in-part of Ser. No. 501,169, Aug. 28, 1974, abandoned.

[52] U.S. Cl. .................................. 260/463; 424/5
[51] Int. Cl.² ...................................... C07C 69/96
[58] Field of Search ................................. 260/463

[56] References Cited

UNITED STATES PATENTS 3,676,486  7/1972  Nikles .............................. 260/463

OTHER PUBLICATIONS

J. Chem. Soc. (B), 1971, pp. 622–627.

*Primary Examiner*—Lewis Gotts
*Assistant Examiner*—D. R. Phillips
*Attorney, Agent, or Firm*—John R. Nesbitt

[57] ABSTRACT

Iodo-aryl carbonates, such as for example, p-iodo-benzyl carbonates, p-iodo-sec-phenethyl carbonates, p-iodo-phenethyl carbonates, p-iodo-phenyl carbonates, 3-(p-iodophenyl)propyl carbonates, 3-(p-iodophenyl)butyl carbonates, 2-(p-iodobenzyl)butyl carbonates and 2-(p-iodobenzyl)-n-hexyl carbonates, for use as radiographic media in connection with such techniques as x-ray applications including myelography, salpingography, lymphography and bronchography. An effective quantity of iodinated organic carbonate provides x-ray contrast, and the compounds of the invention may be characterized generally as carbonates having the general formula

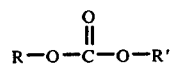

wherein R represents an alkyl group having from 4 to 10 carbon atoms and R' represents an iodinated phenyl linked to the ester oxygen through an alkyl chain consisting of 1 to 3 carbon atoms.

19 Claims, No Drawings

IODINE CONTAINING ORGANIC CARBONATES FOR USE AS RADIOGRAPHIC AGENTS

RELATED APPLICATION

This application is a continuation-in-part of my co-pending U.S. patent application, Ser. No. 501,169, filed Aug. 28, 1974, entitled "Iodone Containing Organic Carbonates For Use As Radiographic Agents", and now abandoned.

FIELD OF THE INVENTION

The present invention relates to contrast media for radiography, and more particularly to the preparation and use of iodinated organic carbonates as contrast media for radiography. More specifically, the present invention relates to the preparation and use as radiographic media of iodinated benzyl carbonates, p-iodo-sec-phenethyl carbonates (sec means secondary or two groups attached to the same carbon atom of the ethyl moiety), p-iodo-phenethyl carbonates, p-iodo-phenyl carbonates, 3-(p-iodophenyl)propyl carbonates, 3-(p-iodophenyl)-butyl carbonates, 2-(p-iodobenzyl)butyl carbonates and 2-(p-iodobenzyl)-n-hexyl carbonates.

PRIOR ART

Myelography and possibly other x-ray applications for body cavities have been performed with iodinated oils. Such radiographic agents after being introduced into the subarachnoid space or other body cavities must be withdrawn because of their incomplete absorption even after periods of several years. Other areas of radiography, including salpingopgrahy, lymphography and bronchography, utilize contrast media which have proven to be irritating, slowly eliminated, produce undesirable side effects, and are difficult to administer. Illustrative prior art compositions for radiography are disclosed in U.S. Pat. No. 3,178,473 issued Apr. 13, 1965 to H.H. Hovik et al. for "Process For The N-alkylation Of Acyl Anilides Halogen Substituted In The Nucleus"; U.S. Pat. No. 2,386,640 issued Oct. 9, 1945 to W.H. Strain et al. for "Bis Esters Of Iodinated Phenyl Aliphatic Carboxylic Acids"; U.S. Pat. No. 3,235,461 issued Feb. 15, 1966 to E. Habicht et al. for "Esters Of 3,5-DIIODO-4-Pyridone-N-Acetic Acid; and U.S. Pat. No. 2,348,231 issued May 9, 1944 to W. H. Strain et al. for "Compounds For Use In Radiography".

OBJECTS OF THE INVENTION

An object of the present invention is to provide new and improved radiographic media which are readily eliminated by the body in a reasonable length of time, which possess low toxicity, which are readily administered, and which demonstrate a minimum of irritating and other undesirable side effects.

Another object of the present invention is to provide new and improved radiographic media having the above characteristics which are suitable for use in x-ray applications including myelography, salpingography, lymphography and bronchography applications.

A further object of the present invention is to provide new and improved radiographic media of the foregoing character which are readily and easily synthesized, are stable and non-toxic.

A still further object of this invention is to provide a new structural linkage, namely the carbonate moiety, as a useful structure for radiopaques.

Other objects and advantages of the present invention will become apparent as the following description proceeds.

SUMMARY OF THE INVENTION

According to the present invention, it has been found that iodinated phenyl carbonates, and particularly p-iodo-benzyl carbonates, p-iodo-sec-phenethyl carbonates, p-iodo-phenethyl carbonates, p-iodo-phenyl carbonates, 3-(p-iodophenyl)propyl carbonates, 3-(p-iodophenyl)butyl carbonates, 2-(p-iodobenzyl)butyl carbonates and 2-(p-iodobenzyl)-n-hexyl carbonates, have many unexpected and valuable properties when used as radiographic media in connection with such current techniques as x-ray applications including myelography, salpingography, lymphography and bronchography. These compounds may be characterized generally as carbonates having the general formula:

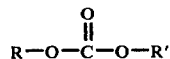

wherein R represents an alkyl group having from 4 to 10 carbon atoms and R' represents iodinated phenyl linked to the ester oxygen through an alkyl chain (which may be a lower alkylene chain) consisting of 1 to 3 carbon atoms. More specifically, the compounds of the present invention may be characterized by the following general formula:

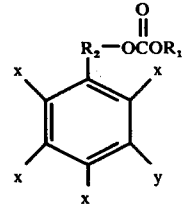

wherein $R_1$ is a lower alkyl group consisting of straight or branched chains having from 4 to 10 carbon atoms, wherein $R_2$ is a lower alkylene chain linking the aromatic ring to the carbonate by 1 to 3 carbon atoms and having attached thereto a constituent selected from the group including hydrogen and alkyl groups with 1 to 4 carbon atoms, $x$ is selected from the group including hydrogen and iodine (1 to 3 iodine), and $y$ is selected from the group including hydrogen, iodine and amine.

In accordance with the present invention, it has been discovered that certain iodinated carbonates exhibit many unexpected and valuable properties when used as radiopaques or radiographic media. Such iodinated carbonates find particular but not necessarily exclusive utility as radiogaphic media for use in x-ray applications including myelography, salpingography, lymphography and bronchography.

In a preferred form, the aromatic ring is substituted primarily by one iodine atom in the para position. Table I shows a number of compounds of the foregoing type which are useful in accordance with the present invention.

Table I
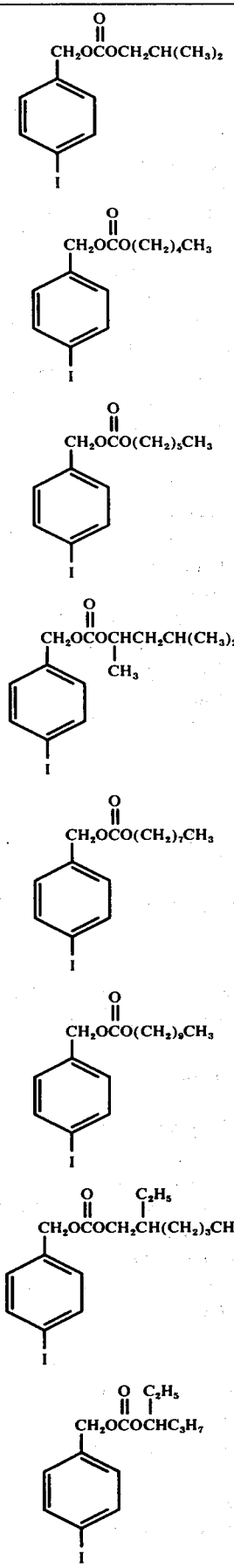
Table I-continued
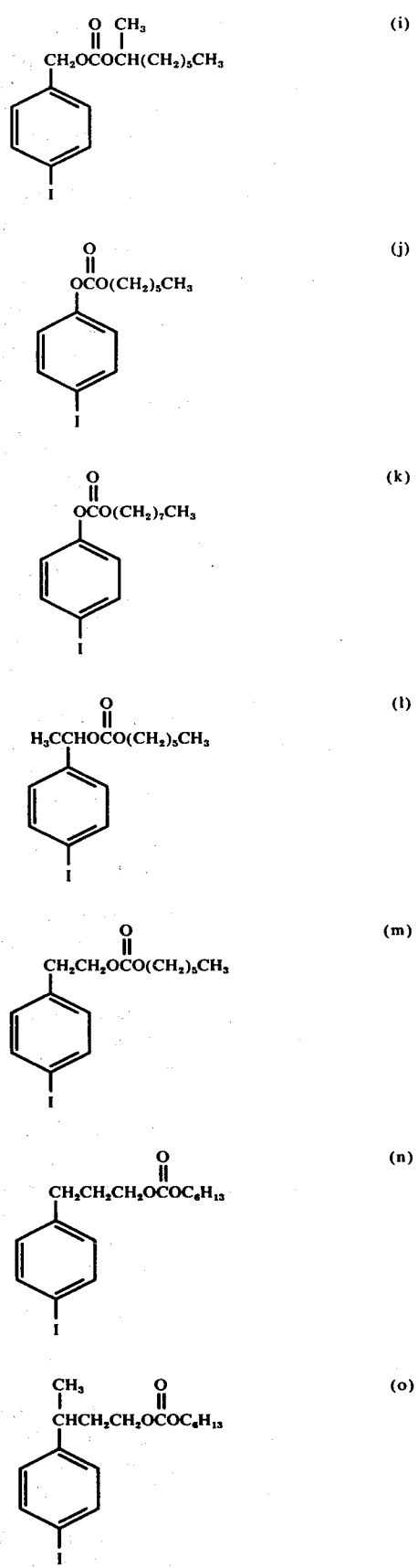

Table I-continued

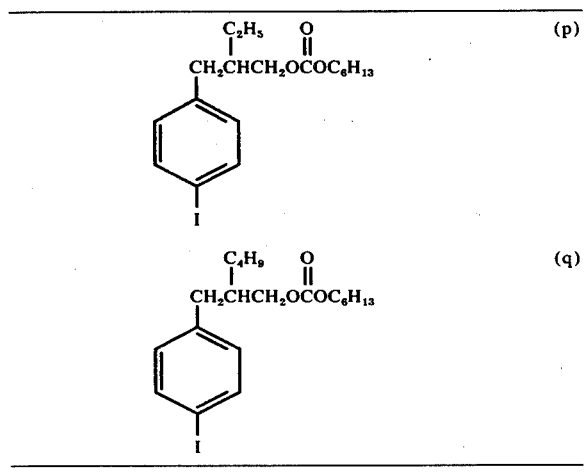

The aromatic ring may also be substituted by an iodine in the meta and/or ortho positions or by more than one iodine or by both iodine and an amine. Examples of such compounds are:

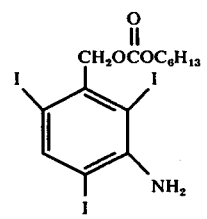

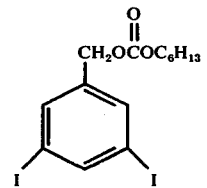

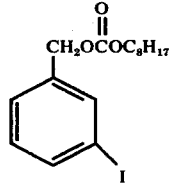

A prior art example of substitution of an aromatic ring by a carbon atom with the carbonate having the general formula as set forth herein above and including R with a single carbon atom is shown by the formula

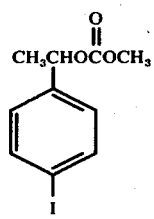

As an initial toxicity screen for the compounds shown herein above, the neat liquid or suspensions of the material was injected into the peritoneal cavity of albino mice and the Approximate Lethal Dose (ALD) determined using the method of Deichmann and Le- Blanc (W.B. Deichmann and T.J. LeBlanc, J. Ind. Hyg., 25, 415 (1943)) the results of which are presented in Table II, as set forth hereinafter.

As can be seen from Table II compound u of the prior art is more toxic and hence structures with a single carbon atom are not suitable for uses contemplated for this invention.

Previous to this invention the carbonate linkage was not an obvious moiety for radiographic use, however, with the success realized with the compounds as set forth in Table I, it follows that the carbonate linkage can be incorporated into still other compounds with particular extensions thereof being listed as follows:

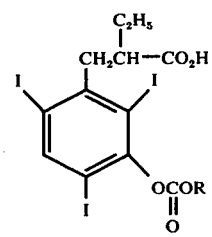

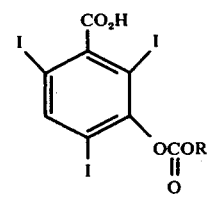

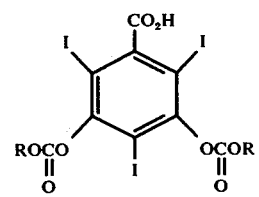

Table II

| Compound No.[a] | Approximate Interperitoneal Toxicity in Mice Approximate Lethal dose Ml/Kg. |
|---|---|
| a | 3 |
| b | 3 |
| c | 7 |
| d | 7 |
| e | 15[b] |
| f | 10.5[b] |
| g | 15 |
| h | 3 |
| i | 15[b] |
| j | 7 |
| k | 7 |
| l | 10.5 |
| m | 7 |
| n | 15 |
| o | 7 |
| p | >15[b] |
| q | >15[b] |
| r | >11[b][c] |
| s | 5 |
| t | >17 |
| u | 1.5 |

[a]See designated formulas herein above for structures.
[b]This was the largest dose administered.
[c]20% w/v in Sesame oil, no deaths seen with neat Sesame oil.

The iodinated carbonates may be synthesized by one of the following procedures, referring to p-Iodobenzyl Carbonates as a representative example:

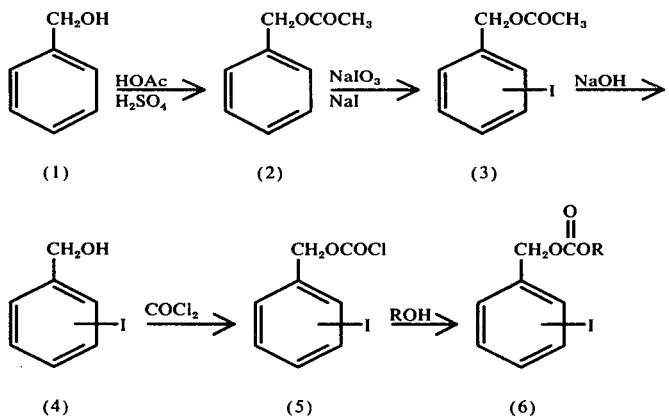

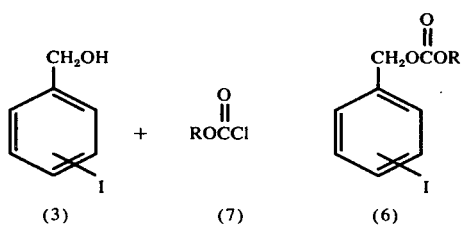

For Preparation of the preferred forms R is as described above.

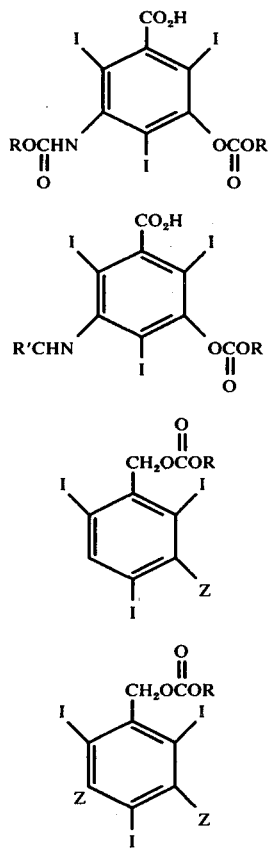

Wherein R has the meaning as indicated above and Z is an amine or lower alkanoyl.

The iodination procedure selected for this invention requires the combination of glacial acetic acid, concentrated sulfuric acid, iodine and sodium iodate. Under these conditions alcohols are converted to acetate esters. For example, in Procedure A treatment of benzyl alcohol with glacial acetic acid and concentrated sulfuric acid forms the acetate ester (2). The simultaneous presence of iodine and sodium iodate gives iodobenzyl acetate (3) in one step. This ester is not isolated but is hydrolized with base to give easily isolated iodobenzyl alcohol (4). The iodinated alcohol is converted to the chloroformate (5) by treatment with phosgene. Conversion of the chloroformate to the desired carbonate (6) is then achieved by addition of the desired alcohol, ROH. For those compounds of Formula I where $R_2$ is sec-phenethyl, the acetate ester is prepared by treating sec-phenethyl alcohol with glacial acetic acid and p-toluene sulfonic acid. The isolated ester is then iodinated by the procedure outlined above. The conversion of the iodinated acetate to the alcohol and the preparation of the carbonates remains the same.

When the alkyl chloroformate (7) is available, compounds of Formula I can be prepared by Procedure II. That is, the alkyl chloroformate (7) in a suitable solvent (e.g. chloroform) is added to the iodinated alcohol (3), thus forming the desired carbonate (6).

The following examples are given as further illustration, but not by way of limitation of the present invention. In these examples, all temperatures are in °C.

EXAMPLE 1 p-Iodobenzyl Alcohol

A solution of glacial acetic acid (1350 ml.) and iodine (250 g.) was heated to 100° and then concentrated sulfuric acid (140 ml. of 95–97%) added, followed by benzyl alcohol (216 g.). Sodium iodate (92 g.) in water (500 ml.) was then introduced dropwise with stirring over a period of 1 hour. The temperature was maintained at 100°–110° for an additional 30 min. before the reaction mixture was poured onto 1 Kg. of crushed ice. The mixture was extracted with chloroform, the combined chloroform solution washed with water, dried, and concentrated. The remaining oil was distilled at reduced pressure to give p-iodobenzyl alcohol. A mass spectrum (70 ev) parent ion was measured at m/e 233.9545; calculated for $C_7H_7IO$, 233.9544. The ir and nmr spectrum were in agreement with the proposed structure. The use of a mass spectrum for identification of compounds is shown, for example, in R. Venkataraghaven, R.D. Broad, R. Klimowsky, J.W. Amy, and F.W. McLafferty, Adv. Mass Spec., 4, 65 (1967) and R. Venkataraghaven, R.J. Klimowksy, F.W. McLafferty, Acc. Chem. Res., 3, 158 (1970).

EXAMPLE 2 p-Iodobenzyl Chloroformate

A three-necked flask was fitted with a gas delivery tube and an exit tube connected to a calcium chloride drying tube. A stirring bar was added. The third neck of the flask was stoppered and the delivery and exit tubes fitted with pinch cocks so that the reaction vessel could be disconnected for weighing. Toluene (100 ml.) was introduced into the flask and the vessel weighed. After cooling to 0° in an ice/salt bath, phosgene was bubbled through the toluene until a weight gain of 30 g. was obtained. p-Iodobenzyl alcohol, (46.2 g.) as prepared in Example 1, in toluene (100 ml.), was then added rapidly. After stirring at 0° and then at room temperature the solution was concentrated by distillation under reduced pressure at a temperature not exceeding 60°. The solution of p-iodo-benzyl chloroformate was stoppered and stored until needed.

EXAMPLE 3 p-Iodobenzyl Carbonates

A three-necked flask was fitted with a thermometer, a drying tube and a dropping funnel containing the p-iodobenzyl chloroformate (0.2 moles) solution prepared as described in Example 2, to which chloroform (300 ml.) had been added. An alcohol (0.8 moles), of the type ROH as described above in Procedure A, was introduced in the flask along with 320 ml. of pyridine and a stirring bar. After cooling to about 0°, the chloroformate solution was added dropwise to the flask while maintaining the temperature below 5°. After adding the chloroformate solution, the reaction mixture was warmed to room temperature and stirred for 1 hour. The reaction mixture and 800 ml. of 6N HCl were added simultaneously with stirring to 400 ml. of 3N HCl in 800 g. of crushed ice. The resulting aqueous phase was extracted with chloroform (3 × 100 ml.). All chloroform phases were combined and backwashed with water (2 × 100 ml.). The chloroform solution was dried with anhydrous magnesium sulfate and concentrated under reduced pressure. Finally, the pure carbonate was obtained by distilling the oil at reduced pressure.

EXAMPLE 4

The carbonate synthesis procedure B was used for this Example. A three-necked flask fitted with a thermometer and an addition funnel was arranged for magnetic stirring. p-Iodobenzyl alcohol (0.3 moles) from Example 1 was dissolved in chloroform (300 ml.) and the solution transferred to the reaction vessel along with pyridine (61 ml.). After cooling in an ice/salt bath, a solution of the desired alkyl chloroformate

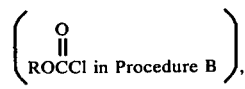

10% excess, in chloroform (175 ml.) was added dropwise while maintaining the temperature below 5°. After completing the addition, the reaction mixture was heated to 50° and held there for 30 min. The reaction mixture was poured into 1 liter of water and extracted with chloroform. The combined chloroform solution was back-washed with water and dried. After removing the chloroform on a rotary evaporator, the oil was distilled at reduced pressures giving the desired carbonate.

EXAMPLE 5 p-Iodobenzyl Isobutyl Carbonate (a of Table I)

The carbonate synthesis of Procedure A was used for this preparation. p-Iodobenzyl chloroformate, in chloroform, was added to a solution of 2-methyl-1-propanol in pyridine. The carbonate was isolated as a colorless oil and had a refractive index of $N_D^{25} = 1.5421$. A mass spectrum (70 ev) parent ion was measured at m/e 334.0064, and calculated for $C_{12}H_{15}IO_3$ at 334.0068. An ir and nmr were in agreement with the proposed structure.

EXAMPLE 6 n-Amyl-p-Iodobenzyl Carbonate (b of Table I)

The carbonate synthesis of Procedure A was used for this preparation. p-Iodobenzyl chloroformate in chloroform was added to a soluton of n-amyl alcohol in pyridine. The isolated n-amyl-p-iodobenzyl carbonate was a colorless oil with a refractive index of $N_D^{25} = 1.5439$. A mass spectrum (70 ev) parent ion was measured at m/e 348.0231, and calculated for $C_{13}H_{17}IO_3$, at 348.0225. An ir and nmr were in agreement with the proposed structure.

EXAMPLE 7 n-Hexyl-p-Iodobenzyl Carbonate (c of Table I)

The carbonate synthesis of Procedure A was used for this preparation. p-Iodobenzyl chloroformate in chloroform was added to a solution of n-hexanol in pyridine. Colorless n-hexyl-p-iodobenzyl carbonate was isolated by distillation and had a refractive index of $N_D^{25} = 1.5368$. A mass spectrum (70 ev) parent ion was measured at m/e 362.0362, and calculated for $C_{14}H_{19}IO_3$ at 362.0381. An ir and nmr were in agreement with the proposed structure.

EXAMPLE 8 p-Iodobenzyl-4-methyl-2-Pentyl Carbonate (d of Table I)

This compound was prepared using the Carbonate Synthesis of Procedure A. p-Iodobenzyl chloroformate was added to a pyridine solution of 2-methyl-4-pentanol. The recovered carbonate was a colorless oil having a refractive index of $N_D^{25} = 1.5320$. A mass spectrum (70 ev) parent ion was measured at m/e 362.0373, and calculated for $C_{14}H_{19}IO_3$ at 362.0381. A ir and nmr were in agreement with the proposed structure.

EXAMPLE 9 n-Octyl-p-Iodobenzyl Carbonate (e of Table I)

The carbonate synthesis of Procedure A was used for this preparation. p-Iodobenzyl chloroformate was added to a solution of n-octyl alcohol in pyridine. Vacuum distillation gave n-octyl-p-iodobenzyl carbonate with a refractive index of $N_D^{25} = 1.5299$. A mass spectrum (70 ev) parent ion was measured at m/e 390.0673, and calculated for $C_{16}H_{23}IO_3$ at 390.0694. An ir and nmr were in agreement with the proposed structure.

EXAMPLE 10 n-Decyl-p-Iodobenzyl Carbonate (f of Table I)

This preparation was carried out using the carbonate synthesis of Procedure A. After adding p-iodobenzyl chloroformate to a pyridine solution of n-octyl alcohol at 0°, the desired n-octyl-p-iodobenzyl carbonate was isolated by vacuum distillation. The colorless, viscous oil had a refractive index of $N_D^{25} = 1.5224$. A mass spectrum (70 ev) parent ion was measured at m/e 418.1002, and calculated for $C_{18}H_{27}IO_3$ at 418.1007. An ir and nmr were in agreement with the proposed structure.

EXAMPLE 11

2-Ethylhexyl-p-Iodobenzyl Carbonate (g of Table I)

The carbonate synthesis of Procedure A was used for this preparation. p-Iodobenzyl chloroformate, in chloroform, was added to a solution of 2-ethyl hexanol in pyridine. The recovered material was vacuum distilled, giving colorless oil with a refractive index of $N_D^{25} = 1.5295$. A mass spectrum (70 ev) parent ion was measured at m/e 390.0661, and calculated for $C_{16}H_{23}IO_3$ at 390.0694. The ir and nmr spectra were in agreement with the proposed structure.

EXAMPLE 12

2-Octyl-p-Iodobenzyl Carbonate (i of Table I)

This compound was prepared from p-iodobenzyl alcohol and 2-octyl alcohol using the carbonate synthesis of Procedure A. Vacuum distillation of the recovered material gave a colorless oil having a refractive index of $N_D^{25} = 1.5259$. A mass spectrum (70 ev) parent ion was measured at m/e 390.0665, and calculated for $C_{16}H_{23}IO_3$ at 390.0694. The ir and nmr spectra were in agreement with the proposed structure.

EXAMPLE 13

3-Hexyl-p-Iodobenzyl Carbonate (h of Table I)

p-Iodobenzyl alcohol and 3-hexanol were reacted as outlined in the carbonate synthesis of Procedure A. The recovered material was distilled to give 3-hexyl-p-iodobenzyl carbonate. The refractive index was $N_D^{25} = 1.5348$. A mass spectrum (70 ev) parent ion was measured at m/e 362.0359, and calculated for $C_{14}H_{19}IO_3$ at 362.0384. The ir and nmr spectra were in agreement with the proposed structure.

EXAMPLE 14 n-Hexyl-p-Iodophenyl Carbonate (j of Table I)

p-Iodophenol reacted with n-hexylchloroformate according to the carbonate synthesis of Procedure B. n-Hexyl-p-iodophenyl carbonate was isolated from the recovered material by vacuum distillation. The compound gave a refractive index of $N_D^{25} = 1.5340$. A mass spectrum (70 ev) parent ion was measured at m/e 348.0210, and calculated for $C_{13}H_{17}IO_3$ at 348.0225. The nmr and ir spectra were in agreement with the proposed structure.

EXAMPLE 15 n-Octyl-p-Iodophenyl Carbonate (k of Table I)

The combination of p-iodophenol with n-octylchloroformate, by means of the carbonate synthesis of Procedure B, gave a crude material containing the desired carbonate. Vacuum distillation successfully separated the carbonate from the starting materials. The colorless oil had a refractive index of $N_D^{25} = 1.5244$. A mass spectrum (70 ev) parent ion was measured at m/e 376.0548, and calculated for $C_{15}H_{21}IO_3$ at 376.0538. The ir and nmr spectra were in agreement with the proposed structure.

EXAMPLE 16 sec-Phenethyl Acetate

A three-necked, round-bottom flask was fitted with a mechanical stirrer and a jacketed tube heated with steam. The top of the steam-heated tube was vented to a water cooled condensor, and the apparatus arranged so that the upper phase of the condensate would return to the round-bottom flask. The flask was charged with 1.4 moles sec-phenethyl alcohol, 120 ml. glacial acetic acid, 250 ml. benzene, and 1.4 grams p-toluene sulfonic acid. After refluxing the reaction mixture for 7 hours, the mixture was extracted with 10% aqueous sodium bicarbonate and water. The benzene solution was then dried with magnesium sulfate and the benzene removed by evaporation. The crude sec-phenethyl acetate was iodinated and hydrolysed using the procedure outlined above for p-iodobenzyl alcohol. Distillation of the recovered material at reduced pressure gave the desired p-iodo-sec-phenethyl alcohol. The isolated material had a refractive index of $N_D^{25} = 1.6046$. A mass spectrum (70 ev) parent ion was measured at m/e 247.9680, and calculated for $C_{18}H_8IO$ at 247.9700. The ir and nmr spectra were in agreement with the proposed structure.

EXAMPLE 17 n-Hexyl-p-Iodo-sec-Phenethyl Carbonate p-Iodo-sec-phenethyl alcohol was treated with n-hexylchloroformate as outlined in the carbonate synthesis of Procedure B. The recovered products were distilled at reduced pressure to give the desired carbonate. The ir and nmr spectra of the oil were in complete agreement with the proposed structure. The refractive index was $N_D^{25} = 1.5265$. A mass spectrum (70 ev) parent ion was measured at m/e 376.0531, and calculated for $C_{15}H_{21}IO_3$ at 376.0538.

EXAMPLE 18 p-Iodophenethyl Alcohol

Phenethyl acetate was converted to p-iodophenethyl alcohol using the procedure outlined for the preparation of p-iodobenzyl alcohol. The isolated material had a refractive index of $N_D^{25} = 1.6155$. The mass spectrum (70 ev) parent ion was measured at m/e 247.9685, and calculated for $C_8H_9IO$ at 247.9700. The ir and nmr spectra were in agreement with the proposed structure.

EXAMPLE 19 n-Hexyl-p-Iodophenethyl Carbonate (m of Table I)

p-Iodophenethyl alcohol was reacted with n-hexyl-chloroformate according to the carbonate synthesis of Procedure B. The isolated material gave an ir and nmr spectra in agreement with the proposed structure. The oil had a refractive index of $N_D^{25} = 1.5295$. The mass spectrum (70 ev) parent ion was measured at m/e 376.0508, and calculated for $C_{15}H_{21}IO_3$ at 376.0538. Analysis: calculated $C_{15}H_{21}IO_3$: C, 47.91; H, 5.63; found C, 48.07; H, 5.66.

EXAMPLE 20 n-Hexyl-3-(p-Iodophenyl)Propyl Carbonate

Preparation of n:

a. 3-Phenyl Propyl Acetate

Using the procedure outlined in Example 16, 3-phenyl propanol was converted to 3-phenyl propyl acetate.

b. 3-(p-Iodophenyl)Propanol

Using the procedure outlined in Example 1, 3-phenyl propyl acetate was converted to 3-(p-iodophenyl)-propanol ($N_D^{25} = 1.6048$).

c. n-Hexyl-3-(p-Iodophenyl)Propyl Carbonate

Using the procedure outlined in Example 4, 3-(p-iodophenyl)propanol was treated with n-hexyl chloroformate giving n ($N_D^{25} = 1.5291$). Mass spectrum (70 ev) parent ion was measured at 390.0708, calculated for $C_{16}H_{23}IO_3$ 390.0694.

EXAMPLE 21 n-Hexyl-3-(p-Iodophenyl)Butyl Carbonate

Preparation of o:

a. 3-Phenyl Butanol

A reaction vessel was fitted with a mechanical stirrer, thermometer and a reflux condenser capped with an additional funnel. While under a positive flow of dry nitrogen, the system was flame dried. The vessel was charged 250 ml of benzene and then 25 gm of aluminum chloride was added as quickly as possible. This mixture was cooled with stirring to 5° C in an ice/salt bath and a solution of 7.2 gm (0.1 mol) of crotyl alcohol in 45 ml of benzene was added dropwise while maintaining the temperature below 5° C. Next, 50 ml of concentrated hydrochloric acid was added cautiously. After warming to room temperature, 50 ml of water was added and the lower organic phase removed. The aqueous portion was then extracted with benzene. The combined organics were washed with aqueous 10% sodium bicarbonate and water. After drying over anhydrous magnesium sulfate, filtering and evaporating, a dark oil was recovered. This was vacuum distilled to give 8.2 gm of colorless 3-phenyl butanol ($N_D^{25} = 1.5210$).

b. 3-(p-Iodophenyl) Butanol

Using the procedure outlined in Example 1, 3-phenyl butanol was converted to 3-(p-iodophenyl)-butanol. Mass spectrum (70 ev) parent ion was measured at 275.9993, calculated for $C_{10}H_{13}IO$ 276.0013.

c. n-Hexyl-3-(p-Iodophenyl)Butyl Carbonate

Using the procedure outlined in Example 4, 3-(p-iodophenyl)butanol was treated with n-hexyl chloroformate giving o. $N_D^{25} = 1.5289$, mass spectrum (70 ev) parent ion was measured at 404.0830, calculated for $C_{17}H_{25}IO_3$ 404.0850.

EXAMPLE 22 n-Hexyl-2-(p-Iodobenzyl)Butyl Carbonate

Preparation of p:

a. α-Ethyl Cinnamic Acid

Benzaldehyde was condensed with potassium butyrate and butyric anhydride according to the procedure as outlined in the patent to Archer, U.S. Pat. No. 2,931,830 to give α-ethyl cinnamic acid, mp 104°–104.8° C.

b. 2-Benzyl Butanoic Acid

A solution of 35.2 gm (0.2 mol) of α-ethyl cinnamic acid in 450 ml of 3% sodium hydroxide was reduced in a hydrogen atmosphere at 60 psi using 4 gm of 5% palladium on charcoal. After hydrogen uptake had ceased, the reaction mixture was filtered, acidified with hydrochloric acid and extracted with ether. Evaporation gave 36 gm (0.2 mol) of 2-benzyl butanoic acid.

c. 2-Benzyl Ethyl Butanoate

A flame dried round-bottom flask was fitted with a condenser capped with a calcium chloride drying tube. A solution of 8.8 gm (0.05 mol) of 2-benzyl butanoic acid and 25 ml of thionyl chloride was refluxed overnight. The excess thionyl chloride was removed at 14 mm of Hg under dry conditions. Next a solution of 20 ml of absolute ethanol in 30 ml of benzene was added and the reaction refluxed for 16 hours. The reaction was then evaporated to an oil, 200 ml water added and this extracted with ether. After drying over magnesium sulfate the ether was removed yielding 10 gm of 2-benzyl ethyl butanoate as a red-brown oil.

d. 2-Benzyl Butanol

A three-necked, round bottom flask was fitted with a mechanical stirrer, addition funnel and reflux condenser. After flame drying the system, 11.7 gm (0.3 mol) of lithium aluminum hydride in 125 ml of anhydrous ether was added and the mixture heated to reflux. The heat was removed and a solution of 38 gm (0.18 mol) of 2-benzyl ethyl butanoate in 75 ml of anhydrous ether was added dropwise at such a rate that refluxing was maintained. The reaction was heated at reflux for an additional 30 minutes and then 45 ml of ethyl acetate added with caution. Next 135 ml of 6 N hydrochloric acid was added, followed by 225 ml of water. The reaction mixture was extracted with ether, the ether dried over anhydrous magnesium sulfate and evaporated to give 29.6 gm (0.17 mol) of crude 2-benzyl butanol.

e. 2-(p-Iodobenzyl)Butanol

Using the procedure outlined in Example 1, 2-benzyl butanol was converted to 2-(p-iodobenzyl)butanol ($N_D^{25} = 1.5886$). Mass spectrum (70 ev) parent ion was measured at 290.0141, calculated for $C_{11}H_{15}IO$ 290.0169.

f. Hexyl-2-(p-Iodobenzyl)Butyl Carbonate

Using the procedure outlined in Example 4, 2-(p-iodobenzyl)butanol was treated with n-hexyl chloroformate to give p ($N_D^{25} = 1.5250$). Mass spectrum (70 ev) parent ion was measured at 418.0994, calculated for $C_{18}H_{27}IO_3$ 418.1007.

EXAMPLE 23 n-Hexyl-2-(p-Iodobenzyl)-n-Hexyl Carbonate

Preparation of q:

a. 2-(p-Iodobenzyl)Hexanol

Using the procedure outlined for the preparation of 2-(p-iodobenzyl)butanol but conducting the initial condensation with benzaldehyde, potassium hexanoate, and hexanoic anhydride, 2-(p-iodobenzyl)-hexanol was recovered ($N_D^{25} = 1.5446$). Mass spectrum (70 ev) parent ion was measured at 318.0470, calculated for $C_{13}H_{19}IO$ 318.0482.

b. n-Hexyl-2-(p-Iodobenzyl)-n-Hexyl Carbonate (q)

Using the procedure outlined in Example 4, 2-(p-iodobenzyl)hexanol was treated with n-hexyl chloroformate giving q ($N_D^{25} = 1.5250$). Mass spectrum (70 ev) parent ion was measured at 446.1320, calculated for $C_{20}H_{31}IO_3$ 446.1320.

EXAMPLE 24

3-Amino-2,4,6-Triiodobenzyl-n-Hexyl Carbonate

Preparation of r:

Using the procedure outlined in Example 4, 3-amino-2,4,6-triiodobenzyl alcohol, prepared according to the procedure set forth by J. Hebky and M. Karasek in Coll. Czech. Chem. Commun., 29, 3103 (1964), was treated with n-hexyl chloroformate. The recovered crude material was dissolved in hot hexane/benzene and after cooling, the solid removed. Evaporation of the mother liquor gave a solid which on recrystallization from ethanol/water gave r (mp 89.6–90.6°).

Anal. ($C_{14}H_{18}I_3NO_3$) C: Calc'd 26.72; found 26.70; H: Calc'd 2.88; found 3.19.

EXAMPLE 25

3,5-Diiodobenzyl-n-Hexyl Carbonate

Preparation of s:

Using the procedure of B. Gaux and D. LeHenaff, Bull. Soc. Chim. Fr. 34, 505 (1974), 2,3,5-triiodobenzoic acid (Aldrich) was treated with lithium aluminum hydride to give 3,5-diiodobenzyl alcohol mp 136.5°–140° (lit 137°). Using the procedure outlined in Example 4, 3,5-diiodobenzyl alcohol was treated with n-hexyl chloroformate giving s ($N_D^{25} = 1.5800$).

Anal. ($C_{14}H_{18}I_2O_3$) C: Calc'd 34.43; found 34.69; H: Calc'd 3.72; found 3.90; I: Calc'd 52.02; found 51.81.

EXAMPLE 26 m-Iodobenzyl-n-Octyl Carbonate

Preparation of t:

Using the procedure outlined in Example 4, m-iodobenzyl alcohol (Aldrich) was treated with n-octyl chloroformate giving t ($N_D^{25} = 1.5232$).

EXAMPLE 27 p-Iodo-sec-Phenethyl Methyl Carbonate

Preparation of u:

Using the procedure outlined in Example 4, p-iodo-sec-phenethyl alcohol was treated with methyl chloroformate giving u ($N_D^{25} = 1.5584$; R. Taylor, J. Chem. Soc. (B) 622 (1971), $N_D^{25} = 1.5611$).

While certain illustrative compounds, compositions, methods and procedures embodying the present invention have been described in considerable detail, it should be understood that there is no intention to limit the invention to the specific forms disclosed. On the contrary, the intention is to cover all modifications, alternative compositions, equivalents and uses falling within the spirit and scope of the invention as expressed in the appended claims.

What is claimed is:

1. A compound of the formula:

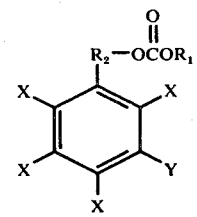

wherein $R_1$ is a lower alkyl group consisting of straight or branched chains having from 4 to 10 carbon atoms, wherein $R_2$ is a lower alkylene chain linking the aromatic ring to the carbonate by 1 to 3 carbon atoms and having attached thereto a constituent selected from the group consisting of hydrogen and alkyl groups with 1 to 4 carbon atoms, X is selected from the group consisting of hydrogen and iodine, and Y is selected from the group consisting of hydrogen, iodine and amine when X is iodine and is iodine when X is hydrogen.

2. The compound of claim 1 wherein said compound is p-iodobenzyl isobutyl carbonate.

3. The compound of claim 1 wherein said compound is n-amyl-p-iodobenzyl carbonate.

4. The compound of claim 1 wherein said compound is n-hexyl-p-iodobenzyl carbonate.

5. The compound of claim 1 wherein said compound is p-Iodobenzyl-4-methyl-2-pentyl carbonate.

6. The compound of claim 1 wherein said compound is n-octyl-p-iodobenzyl carbonate.

7. The compound of claim 1 wherein said compound is n-decyl-p-iodobenzyl carbonate.

8. The compound of claim 1 wherein said compound is 2-ethylhexyl-p-iodobenzyl carbonate.

9. The compound of claim 1 wherein said compound is 2-octyl-p-iodobenzyl carbonate.

10. The compound of claim 1 wherein said compound is 3-hexyl-p-iodobenzyl carbonate.

11. The compound of claim 1 wherein said compound is m-iodobenzyl-n-octyl carbonate.

12. The compound of claim 1 wherein said compound is 3,5-diiodobenzyl-n-hexyl carbonate.

13. The compound of claim 1 wherein said compound is 3-amino-2,4,6-triiodobenzyl-n-hexyl carbonate.

14. The compound of claim 1 wherein said compound is n-hexyl-p-iodo-sec-phenethyl carbonate.

15. The compound of claim 1 wherein said compound is n-hexyl-p-iodophenethyl carbonate.

16. The compound of claim 1 wherein said compound is n-hexyl-3-(p-iodophenyl)propyl carbonate.

17. The compound of claim 1 wherein said compound is n-hexyl-3-(p-iodophenyl)butyl carbonate.

18. The compound of claim 1 wherein said compound is n-hexyl-2-(p-iodobenzyl)butyl carbonate.

19. The compound of claim 1 wherein said compound is n-hexyl-2-(p-iodobenzyl)-n-hexyl carbonate.

* * * * *